United States Patent
Backensfeld et al.

(10) Patent No.: US 6,610,670 B2
(45) Date of Patent: Aug. 26, 2003

(54) CYCLODEXTRIN-DROSPIRENONE INCLUSION COMPLEXES

(75) Inventors: Thomas Backensfeld, Berlin (DE); Wolfgang Heil, Berlin (DE)

(73) Assignee: Schering Aktiengesellschaft, Berlin (DE)

( * ) Notice: Subject to any disclaimer, the term of this patent is extended or adjusted under 35 U.S.C. 154(b) by 0 days.

(21) Appl. No.: 10/022,846

(22) Filed: Dec. 20, 2001

(65) Prior Publication Data

US 2002/0128229 A1 Sep. 12, 2002

Related U.S. Application Data

(60) Provisional application No. 60/256,483, filed on Dec. 20, 2000.

(30) Foreign Application Priority Data

Dec. 20, 2000 (EP) ............................................. 00610134

(51) Int. Cl.[7] ...................... A01N 43/04; A61K 31/715
(52) U.S. Cl. ........................... 514/58; 514/54; 514/167; 514/169; 514/171; 514/172; 514/843; 536/102; 536/103; 536/123.1
(58) Field of Search ........................... 514/54, 58, 843, 514/167, 169, 171, 172; 536/102, 103, 123.1

(56) References Cited

U.S. PATENT DOCUMENTS

| 4,129,564 | A | | 12/1978 | Wiechert et al. | |
|---|---|---|---|---|---|
| 4,596,795 | A | | 6/1986 | Pitha | |
| 4,727,064 | A | | 2/1988 | Pitha | |
| 5,376,641 | A | | 12/1994 | Ammeraal | |
| 5,824,667 | A | * | 10/1998 | Spona et al. | 514/170 |
| 5,885,978 | A | | 3/1999 | Yamada et al. | |
| 5,888,543 | A | * | 3/1999 | Gast | 424/464 |
| 6,346,518 | B1 | * | 2/2002 | Heeres et al. | 514/58 |

FOREIGN PATENT DOCUMENTS

| DE | 2652761 | 11/1976 |
|---|---|---|
| EP | 398460 A2 | 5/1990 |
| FR | 2515187 A1 | 10/1982 |
| WO | WO 96/02277 | 2/1996 |

OTHER PUBLICATIONS

K. Uekama, Inclusion complexations of steroid hormones with cyclodextrins in water and in solid phase, Elsevier Biomedical Press, 1982.
K. Kralova, Interactions of β–cyclodextrin with steroid compounds in aqueous solutions, Pharmazie, 1989.
W.A.J.J. Hermens, Delivery of hormones: some new concepts, Pharmaceutisch Weekblad Scientific Edition, 1992.
Rolf Krattenmacher, Drospirenone: pharmacology and pharmacokinetics of a unique progestogen, Elsevier Science Inc., 2000.
J.P. Norman, Contraceptive Hormone Replacement therapy Aldosterone Antagonist Progestogen, Drugs of the Future, 2000.
K. Uekama, Cyclodextrin inclusion compounds:effects on Stability and Bio–Pharmaceutical Properties, Elsevier Science, 1987.
Kaneto Uekama, Cyclodextrin Drug Carrier Systems, Chemical Reivew, 1998.

* cited by examiner

*Primary Examiner*—James O. Wilson
*Assistant Examiner*—Patrick Lewis
(74) *Attorney, Agent, or Firm*—Millen, White, Zelano & Branigan, P.C.

(57) ABSTRACT

Described are inclusion complexes formed between cyclodextrin and drospirenone. In a specific embodiment of the invention, the cyclodextrin is β-cyclodextrin. The invention further relates to methods of providing such an inclusion complex, and to the use of said inclusion complex for improving the solubility of drospirenone, for providing pharmaceutical compositions, for use as a medicament in the treatment of symptoms associated with menopause and in female contraception.

34 Claims, 1 Drawing Sheet

β- cyclodextrin

Drospirenone

CYCLODEXTRIN-DROSPIRENONE INCLUSION COMPLEXES

This application claims priority to U.S. Provisional Application No. 60/256,483, filed Dec. 20, 2000.

FIELD OF INVENTION

The present invention relates to an inclusion complex formed between cyclodextrin and drospirenone, to methods of providing such an inclusion complex, and to a method of increasing the water solubility of drospirenone by providing such an inclusion complex. Moreover, the present invention relates to the use of said inclusion complex in pharmaceutical compositions for use as a medicament in the treatment of symptoms associated with menopause and in female contraception.

BACKGROUND OF THE INVENTION

Drospirenone (6β,7β;15β,16β-dimethylene-3-oxo-17α-pregn-4-ene-21,17-carbolactone), which may be prepared substantially as described in e.g. U.S. Pat. No. 4,129,564 or WO 98/06738, is only sparingly soluble in aqueous media at various pH values.

The water solubility of a compound is extremely pertinent with regards to its utility in industry, particularly in the pharmaceutical industry where there is a strong link between water solubility and bioavailability. The therapeutic efficiency of drospirenone may be improved by increasing its overall water solubility, thus providing for routes of administration alternative to those proceeding via the gastrointestinal tract, where absorption is slow and then rapidly cleared from circulating blood by the liver.

Cyclodextrins are known to solubilize nonpolar compounds and improve the absorption of certain compounds by forming complexes with said compounds. The cyclodextrins are frequently derivatized in order to improve the solubility or to accommodate appropriately the compound of interest. However, certain compounds are not well accommodated by the cavity of the some of the cyclodextrin molecules.

Drospirenone, in its uncomplexed form, is known from DE 26 52 761 in which its use as a diuretic compound is disclosed.

U.S. Pat. No. 4,596,795 discloses a complex between α-, β- and γ-cyclodextrins and derivatives thereof with testosterone, progesterone, and estradiol and the solubility of said complexes.

U.S. Pat. No. 5,885,978 relates to a composition comprising an adrenal cortical steroid and cyclodextrin prepared by clathrating the adrenal cortical steroid in the cyclodextrin using a homomixer.

U.S. Pat. No. 5,376,641 discloses a method of making a steroid water soluble by mixing a steroid and a branched beta cyclodextrin together in water for a period of 4 to 24 hours under ambient conditions.

U.S. Pat. No. 5,376,641 discloses a method for making a steroid water soluble by complexing the steroid with branched β-cyclodextrin.

U.S. Pat. No. 4,727,064 discloses a method of improving the dissolution properties of a steroid by forming a solid comprising at least one of testosterone, progesterone and estradiol as an inclusion complex with a poly-β-cyclodextrin and /or hydroxypropyl-β-cyclodextrin adapted for administration by buccal route.

FR 2 515 187 discloses inclusion complexes between γ-cyclodextrines and various steroids, such as a spironolactone steroid.

WO 96/02277 discloses pharmaceutical compositions containing cyclodextrin-clathrate complexes of steroid sexual hormones for protection against oxidative degradation of steroids.

SUMMARY OF THE INVENTION

The invention relates to an inclusion complex between cyclodextrin and 6β,7β;15β,16β-dimethylene-3-oxo-17α-pregn-4-ene-21,17-carbolactone (drospirenone).

The invention also relates to methods for producing an inclusion complex between cyclodextrin and drospirenone comprising combining drospirenone and cyclodextrin at a molar ratio of from 0.3:1 to 20:1, preferably 1:1, 2:1, 3:1, 4:1 or 5:1, most preferably 2:1 or 3:1, particularly 3:1.

One object of the present invention is to increase the water-solubility of drospirenone. The present invention thus further relates to methods for improving the solubility of drospirenone, said method comprising forming an inclusion complex between drospirenone and cyclodextrin.

In a further aspect of the invention, pharmaceutical compositions comprising an inclusion complex of drospirenone and cyclodextrin are anticipated. Consequently, the use of the inclusion complex between drospirenone and cyclodextrin as a medicament and for the preparation of a composition for female contraception or for the treatment of menopausal symptoms are defined herein. Upon further study of the specification and appended claims, further objects and advantages of this invention will become apparent to those skilled in the art.

DETAILED DESCRIPTION OF THE INVENTION

The term "inclusion complex" is intended to mean a complex wherein at least a moiety of drospirenone has inserted itself, at least partially, into the cavity of cyclodextrin.

In efforts to improve the functional utility of drospirenone, research has led to a new chemical entity, an inclusion complex between cyclodextrin and drospirenone. The cyclodextrin, may be selected from α-cyclodextrin, β-cyclodextrin, γ-cyclodextrin or derivatives thereof. Preferred embodiments of the present invention are that of a complex between drospirenone and β-cyclodextrin or derivatives thereof or a complex between drospirenone and γ-cyclodextrin or derivatives thereof, most preferably a complex between drospirenone and β-cyclodextrin or γ-cyclodextrin, particularly β-cyclodextrin.

The cyclodextrin, as stated, may be selected from the group comprised of α-cyclodextrin, β-cyclodextrin or γ-cyclodextrin, i.e. the 6-, 7-, or 8-sugar unit macrocycle, respectively. The cyclodextrin may be modified such that some or all of the primary or secondary hydroxyls of the macrocyle, or both, may be alkylated or acylated. Methods of modifying these alcohols are well known to the person skilled in the art and many derivatives are commercially available. The cyclodextrin may be modified such that one or more of the primary or secondary hydroxyls of the macrocyle, or both, may be alkylated or acylated. Methods of modifying these alcohols are well known to the person skilled in the art and many are commercially available. Thus, some or all of the hydroxyls of cyclodextrin may be substituted with an O—R group or an O—C(O)—R, wherein R is an optionally substituted $C_{1-6}$ alkyl, an optionally substituted $C_{2-6}$ alkenyl, an optionally substituted $C_{2-6}$ alkynyl, an optionally substituted aryl or heteroaryl group. R may be methyl, ethyl, propyl, butyl, pentyl, or hexyl group. Consequently, O—C(O)—R may be an acetate. Furthermore, R may be such as to derivatize cyclodextrin with the commonly employed 2-hydroxyethyl group, or 2-hydroxypropyl group. Moreover, the cyclodextrin alcohols may be per-benzylated, per-benzoylated, or benzylated or benzoylated on just one face of the macrocycle, or wherein only 1, 2, 3, 4, 5, or 6 hydroxyls are benzylated or benzoylated. The hydroxyl groups of cyclodextrin may be per-alkylated or per-acylated such as per-methylated or per-acetylated, or alkylated or acylated, such as methylated or acetylated, on just one face of the macrocycle, or wherein only 1, 2, 3, 4, 5, or 6 hydroxyls are alkylated or acylated, such as methylated or acetylated.

In a preferred embodiment of the invention, the inclusion complex is between β-cyclodextrin or γ-cyclodextrin and drospirenone. Most preferably, the inclusion complex is between β-cyclodextrin and drospirenone and in a further interesting embodiment thereof, the β-cyclodextrin is unmodified.

One or more drospirenone molecules may be included into the cavity of the cyclodextrin molecule. Conversely, one molecule of drospirenone may be included into the cavity of one or more cyclodextrin molecules. The inclusion complex may exist in a variety of molar ratios. The molar ratio between drospirenone and the cyclodextrin is dependent on a variety of physical factors during the formation of the inclusion complex. Furthermore, the molar ratio of the inclusion complex may be transitional and vary during its preparation. Given the inclusion of drospirenone can result from a variety of interactions with any number of functional groups or moieties of drospirenone, the depth at which drospirenone is included within the cavity of a cyclodextrin may vary. Furthermore, the size of the cavity, which depends on the selection of cyclodextrin (α-cyclodextrin, β-cyclodextrin or γ-cyclodextrin) and on whether the numerous free hydroxyl groups present on the periphery of the cavity of a cyclodextrin molecule are partially or fully derivatized, will influence the ability for drospirenone to include itself into the cavity. These factors, amongst others, influence the molar ratio of the inclusion complex.

Without being limited to a particular manner in which the inclusion complex is formed, it is presumed that the inclusion complex is an inclusion complex wherein hydrophobic interactions favour the inclusion of hydrophobic moieties from drospirenone into the cavity of a cyclodextrin molecule, given the relative hydrophobicity of the numerous alkyl groups in the cavity of the cyclodextrin.

Given the above-stated factors, and that the moiety of the drospirenone molecule which may include itself into the cyclodextrin molecule may vary, the molar ratio between drospirenone and the cyclodextrin, respectively, may be 1:1, 2:1, 3:1, 3:2, 1:2, 2:2, 2:3 or 1:3. Preferably a 1:1 or 1:2 molar ratio exists between drospirenone and cyclodextrin; namely, one molecule of drospirenone, or a moiety thereof, is at least partially inserted into the cavity of one cyclodextrin molecule or one molecule of drospirenone, or moieties thereof, is at least partially inserted into the cavity of two molecules of cyclodextrin. Alternatively, a 2:1 molar ratio may exist between drospirenone and cyclodextrin; namely, two molecules of drospirenone, or moieties thereof, are at least partially inserted into the cavity of one cyclodextrin molecule.

The term "solubility" in connection with drospirenone is intended to mean the solubility of the inclusion complex between drospirenone and cyclodextrin in water. The term "total solubility" relates to the drospirenone concentration in a phase solubility isotherm, namely to the solubility of uncomplexed and complexed drospirenone. The "total solubility" is a function of the cyclodextrin concentration.

Given one of the objects of the present invention is to increase the solubility and total solubility of drospirenone, it is preferred that the inclusion complex is such that the total water solubility of drospirenone at 20° C. is increased by a factor of at least 2, such as at least 2.5, at least 3, at least 3.5, or at least 4 compared to drospirenone in an uncomplexed form.

Correspondingly, it is preferred that the total solubility of drospirenone in water at 20° C. is increased to at least $9 \times 10^{-5}$ mol/L, such as at least $1 \times 10^{-4}$ mol/L, $2 \times 10^{-4}$ mol/L, $3 \times 10^{-4}$ mol/L or $3.5 \times 10^{-4}$ mol/L.

The inclusion complex may exist in the form of a hydrate containing varying amounts of water, such as between about 1% and 25% water. The degree of hydration may vary according to, amongst other reasons, the degree of substitution of the hydroxyls, the method of preparation and the molar ratio of the inclusion complex. The water content of the inclusion complex may depend on the manner in which the inclusion complex is stored, the temperature, pressure and relative humidity. Thus, any discussion on the solid state form of the drospirenone-cyclodextrin inclusion complex comprises the range of hydrates. The hydrate water is part of the crystal lattice and thus modifying the water content may change the crystal lattice and possibly some of the physical properties of the inclusion complex.

As is known to the person skilled in the art, cyclodextrin itself forms an inclusion complex with water. Thus, the cyclodextrin used in the preparation of the drospirenone-cyclodextrin inclusion complex may be in a hydrated form or in an anhydrous form.

A further object of the invention is to provide a method for producing an inclusion complex comprising the step of combining cyclodextrin and drospirenone at a molar ratio of from 0.3:1 to 20:1, preferably 1:1, 2:1, 3:1, 4:1 or 5:1, most preferably 2:1 or 3:1, particularly 3:1.

The term "solution" in connection with cyclodextrin or drospirenone and in connection with the preparation of an inclusion complex is intended to comprise embodiments wherein the solute, namely cyclodextrin or drospirenone, is fully or partially dissolved in the solvent so as to form a homogenous solution, a saturated solution, a super-saturated solution, a slurry or a suspension.

In the preparation of the inclusion complex according to the present invention, the combining of the components may be done using a solution of cyclodextrin, comprising organic solvent or an aqueous solution such as water. In some embodiments of the invention, the solvent comprises a mixture of water and an organic solvent. The organic solvent may be selected from any of those commonly used in organic synthesis such as, but not limited to, THF, methylene chloride, diethyl ether, petroleum ether, ethyl acetate, dioxane, DMF, DMSO, acetone, acetonitrile, ethanol, methanol, pyridine, or combinations thereof. Preferably, the organic solvent is miscible with water. Polar solvents are preferred such as water, methanol, ethanol, DMSO, DMF, and pyridine, most preferably water or ethanol, particularly water.

A solution of cyclodextrin, as described supra, in any concentration or degree of homogeneity, may be combined with solid drospirenone. Alternatively, the cyclodextrin solution may be combined with a solution of drospirenone. In the embodiment where a solution of cyclodextrin is combined with solid drospirenone, drospirenone may be in its micronized form.

In the embodiment where a solution of cyclodextrin is combined with a solution of drospirenone, drospirenone may be fully or partly dissolved in an organic solvent or water. Organic solvents may be selected from any of those known to the person skilled in the art such as, but not limited to, THF; methylene chloride, diethyl ether, petroleum ether, ethyl acetate, dioxane, DMF, DMSO, acetone, acetonitrile, ethanol, methanol, pyridine, or combinations thereof.

It follows that a solution of drospirenone, as described supra, in any degree of homogeneity and in any concentration may be combined with solid cyclodextrin in the preparation of an inclusion complex between cyclodextrin and drospirenone.

Alternatively, solid drospirenone and solid cyclodextrin may be combined in their solid forms and then combined with water or an organic solvent.

In a preferred embodiment of the invention, a method of producing an inclusion complex comprises the steps of dissolving cyclodextrin in water, optionally with the aid of heating, to form a cyclodextrin solution; dissolving drospirenone in a solvent selected from the group comprising of water and ethanol or mixtures thereof, optionally with the aid of heating, to form a drospirenone solution; combining the cyclodextrin solution and the drospirenone solution to form a combined solution; stirring the combined solution, preferably while keeping the solution at or below 25° C.; filtering the resultant precipitate; washing the precipitate with a solvent selected from the group consisting of water, ethanol, ether and acetone, preferably wherein the solvent is cooled to below 25° C.; optionally suspending the resultant solid in a solvent, preferably acetone, and washing the suspended material with a solvent selected from the group consisting of water, ethanol, ether and acetone, preferably wherein the solvent is cooled to below 25° C.; removing substantially all of the solvent from the solid material. Preferably, the solvent is removed by spray drying or alternatively by lyophilization.

The method of preparation may further comprise mechanical mixing, agitation or shaking, or heating of the solutions or combined components.

In embodiments of the invention wherein an organic solvent is used in the combination of drospirenone or cyclodextrin, the inclusion complex formed may contain one or more molecules of said solvents, depending on the method of drying, precipitation or crystallisation. The complex may alternatively exist in the form of a hydrate containing varying amounts of water.

A typical preparation of the drospirenone-cyclodextrin inclusion complex may be as follows: Drospirenone is dissolved in a solvent such as acetone or ethanol. The cyclodextrin is dissolved in water between 20 and 100° C., such as between 30 and 90° C., such as between 40 and 80° C., preferably between 40 and 60° C., such as at or near 40° C., 45° C., 50° C., 55° C. or 60° C. The drospirenone solution is added to the cyclodextrin solution and the obtained suspension is stirred at 20-30° C. for some hours, such as about 0.5 to 48 hours, then stirred at 2° C. for some hours. The crystallised product is isolated and dried. In an alternative process, the drospirenone solution is added to the cyclodextrin solution and the obtained suspension is stirred at temperatures below 25° C.

The inclusion complex may be prepared by methods described in or similar to those described in Examples 2, 3, 4, and 5.

The crystallised product may be washed with water, acetone and/or any other solvent in order to wash off non-complexed material. The solvent used to wash the crystallised product may be pre-cooled to below 25° C. This crystallised product may be dried over a drying agent such as $P_2O_5$ or any other known to the person skilled in the art in a vacuum dessicator or cabinet for several hours or days. It may also be cooled in the dessicator during drying, or undergo spray drying or lyophillization.

A further objective of the invention is to provide a pharmaceutical composition comprising an inclusion complex of drospirenone and cyclodextrin as described supra together with one or more pharmaceutically acceptable carriers or excipients. The pharmaceutical composition may be adapted to be administered by oral, parental, mucosal, or topical, vaginal, subcutaneous or nasal administration. The composition may comprise from 0.1 mg to 10 mg of drospirenone, depending on its therapeutic application.

The drospirenone cyclodextrin inclusion complex may be used as a medicament. The drospirenone cyclodextrin inclusion complex may be used for the preparation of a pharmaceutical composition for female contraception or for the treatment of menopausal symptoms.

In suitable embodiments of the present invention, a pharmaceutical composition may comprise an inclusion complex between drospirenone and cyclodextrin and further comprise one or more therapeutically active substances. The therapeutically active substance is preferable a steroid. The therapeutically active substance may be complexed with cyclodextrin. Moreover, it may form part of an inclusion complex further comprising drospirenone. For instance, in the embodiment wherein drospirenone and cyclodextrin form an inclusion complex with a 1:2 or 1:3 molar ratio, respectively, said inclusion complex may further comprise a therapeutically active substance to form an inclusion complex with a 1:2:1 or 1:3:1. Alternatively, said therapeutically active substance may be provide not as part of an inclusion complex. The pharmaceutical composition may comprise a drospirenone cyclodextrin inclusion complex, a therapeutically active substance such as estrogen or progestogen or a gestagen together with one or more pharmaceutically acceptable carriers or excipients.

Thus, one embodiment of the present invention is a three-component inclusion complex comprising drospirenone, one or more therapeutically active substances and cyclodextrin. The three-component complex may, for example, comprise drospirenone, cyclodextrin and a therapeutically active substance in molar ratio of 1:1:1, 1:2:1, 1:3:1, 2:2:1, 2:3:1, 2:3:2, 1:3:2. The molar ratio is limited in part by the size cavity of the cyclodextrin, by the nature of the active substance and by the size of moieties included into the cavity.

Three component complexes may be prepared by combining the therapeutically active substance in solid or solution form with either a solid or solution form of drospirenone, a solid or solution form of cyclodextrin, a solid mixture of cyclodextrin and drospirenone, or with a solution of cyclodextrin and drospirenone, namely the combined solution.

The entire disclosures of all applications, patents and publications, cited herein, and of U.S. Provisional Application Serial No. 60/256,483, filed Dec. 20, 2000, and of EP Application No. 00610134.9, filed Dec. 20, 2000, are hereby incorporated by reference.

BRIEF DESCRIPTION OF THE EXAMPLES

Example 1 compares the solubility of drospirenone in water with the solubility of a sample of an inclusion complex substantially consisting of a 1:1 molar ratio between β-cyclodextrin and drospirenone and to a sample consisting substantially of a 2:1 molar ratio between β-cyclodextrin and drospirenone. The example illustrates the increase in solubility of drospirenone by complexation with β-cyclodextrin. The example further discloses the stability of the 1:1 complex.

Examples 2 and 5 disclose two alternative methods for the preparation of a complex between drospirenone and γ-CD.

Examples 3 and 4 disclose two alternative methods for the preparation of a complex between drospirenone and β-CD.

EXAMPLES

Figure 1:
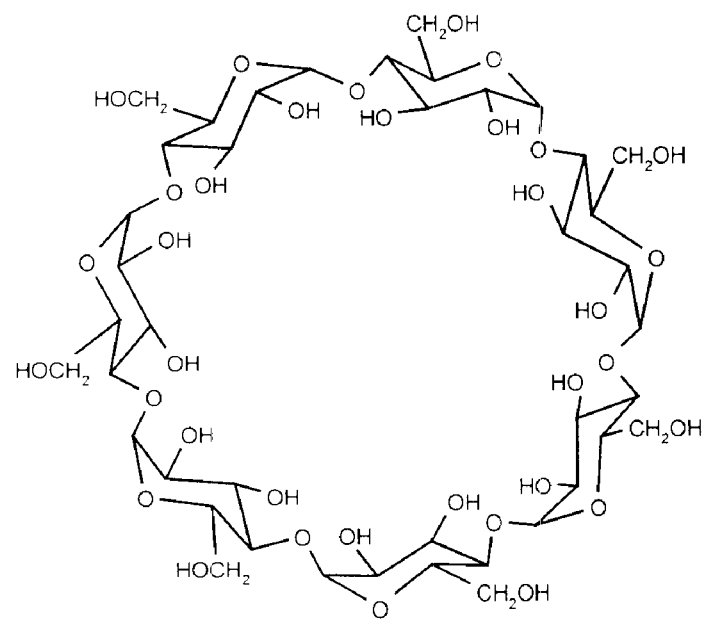
FIG. 1 represents the structure of drospirenone and an embodiment of another component of the inclusion complex, cyclodextrin, namely β-cyclodextrin. β-cyclodextrin is a macrocycle consisting of 7 sugar units, whereas γ-cyclodextrin is a macrocycle consisting of 8 sugar units.
Figure 1:
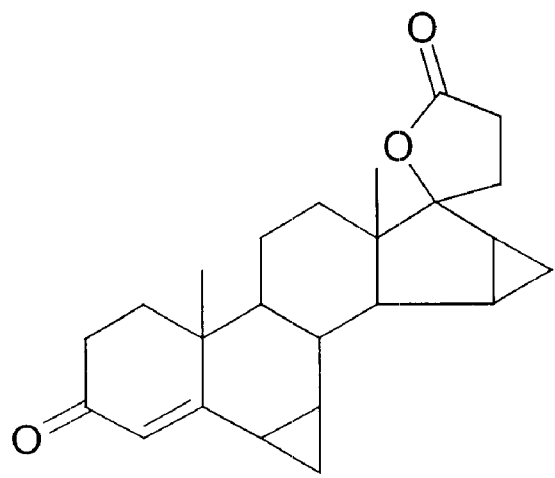

The foregoing and in the following examples are not a limitation upon the invention. In the examples, all temperatures are set forth uncorrected in degrees Celsius; and, unless otherwise indicated, all parts and percentages are by weight.

Example 1

Solubility of Drospirenone

The following data were obtained with the phase solubility diagram technique (PSD) In aqueous solutions at 20° C. The stability constants of the inclusion compound from β-CD and drospirenone are given.

| | |
|---|---|
| Stability constant of the 1:1 complex | $K_{1:1} = 2.2 \times 10^{-4}$ M$^{-1}$ |
| Solubility of Drospirenone | $S_{DP} = 4.14 \times 10^{-5}$ mol/L (1.51 × 10$^{-2}$ g/L) |
| Solubility of 1:1 complex | $S_{1:1} = 3.88 \times 10^{-4}$ mol/L (0.516 g/L) |
| Solubility of 1:2 complex | $S_{1:2} = 3.79 \times 10^{-5}$ mol/L (0.1 g/L) |

Example 2

Preparation of a Complex Between Drospirenone and γ-CD 30 mmol of the cyclodextrin are dissolved in 900 mL of water at 45° C. and, over the course of 30 min., 10 mmol of drospirenone, dissolved in 130 mL of ethanol are added dropwise. After washing with a further 5 mL of ethanol, cooling to room temperature, stirring at room temperature for 24 h and stirring in an ice bath (2° C.) for 4 h, the precipitate was filtered off with suction on a G4 frit. The resulting complex was then washed twice with 100 mL of ice water each time and once with 50 mL of ice-cooled acetone. It is then dried in a dessicator over phosphorous pentoxide.

Example 3

Preparation of a Complex Between Drospirenone and β-CD 24 mmol of the cyclodextrin are dissolved in 970 mL of water at 45° C. and, over the course of 30 min, 8 mmol of drospirenone, dissolved in 90 mL of ethanol are added dropwise. After washing with a further 5 mL of ethanol, cooling to room temperature, stirring at room temperature for 22 h and stirring in an ice bath (4° C.) for 3 h, the precipitate was filtered off with suction on a G4 frit. The resulting complex was then washed twice with 100 mL of ice water each time and twice with 50 mL of ice-cooled acetone. It is then dried in a dessicator over phosphorous pentoxide.

Example 4

Preparation of a Complex Between Drospirenone and β-CD 15.5 g of β-CD are dissolved in 1000 mL of water, heating if necessary. 1.468 g of drospirenone are weighed into the aqueous cyclodextrin solution. The suspension is stirred at room temperature for 72 h. It is then stirred at +2° C. for 3 h. The solid is filtered off with suction on a G4 frit and washed twice with 100 mL of water each time. The crystals are twice suspended in 50 mL of acetone and filtered off with suction each time. They are then washed with 100 mL of water. The moist crystals are dried in vacuo over phosphorous pentoxide.

Example 5

Preparation of a Complex Between Drospirenone and γ-CD 21.38 g of γ-CD are dissolved in 1000 mL of water, heating if necessary. 1.83 g of drospirenone are weighed into the aqueous cyclodextrin solution. The suspension is stirred at room temperature for 72 h. It is then stirred at +2° C. for 3 h. The solid is filtered off with suction on a G4 frit and washed twice with 100 mL of water each time. The crystals are twice suspended in 50 mL of acetone and filtered off with suction each time. They are then washed with 100 mL of water. The moist crystal are dried in vacuo over phosphorous pentoxide.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. An inclusion complex comprising cyclodextrin and drospirenone.

2. The inclusion complex according to claim 1, wherein the cyclodextrin is selected from the group consisting of α-cyclodextrin, β-cyclodextrin, γ-cyclodextrin and derivatives thereof wherein derivatives are derivatized by being alkylated, acylated, benzylated, or benzoylated at some or all of the primary or secondary hydroxyls of the macrocycle.

3. The inclusion complex according to claim 2, wherein the cyclodextrin is β-cyclodextrin or γ-cyclodextrin.

4. The inclusion complex according to claim 3, wherein the cyclodextrin is β-cyclodextrin.

5. The inclusion complex according to claim 1, wherein the inclusion complex comprising drospirenone and the cyclodextrin is in a molar ratio, respectively, selected from the group consisting of 1:1, 2:1, 3:1, 3:2, 1:2, 2:2, 2:3 and 1:3.

6. The inclusion complex according to claim 5, wherein the ratio is 1:1, 2:1 or 1:2.

7. The inclusion complex according to claim 1 further comprising one or more therapeutically active substances, other than drospirenone.

8. A method for producing an inclusion complex of claim 1 comprising combining cyclodextrin and drospirenone at a molar ratio of, respectively, from 0.3:1 to 20:1.

9. The method of claim 8, wherein the ratio is 1:1, 2:1, 3:1, 4:1 or 5:1.

10. The method of claim 8, wherein the ratio is 2:1 or 3:1.

11. The method according to claim 8, comprising the combining of a solution of drospirenone with a solution of cyclodextrin.

12. The method according to claim 8, comprising the combining of solid drospirenone with a solution of cyclodextrin.

13. The method according to claim 8, wherein the cyclodextrin is in a solution comprising a solvent selected from the group consisting of water, ethanol, acetone, acetonitrile, methanol, DMSO, pyridine and combinations thereof.

14. The method of claim 13, wherein the solution comprises water.

15. The method according to 8, wherein the drospirenone is in a solution comprising a solvent selected from the group consisting of water, ethanol, acetone, acetonitrile, methanol, DMSO, pyridine and combinations thereof.

16. The method of claim 15, wherein the solution comprises water, ethanol or both.

17. The method according to claim 8 comprising;
dissolving cyclodextrin in water, optionally with heating, to form a cyclodextrin solution;
dissolving drospirenone in a solvent selected from the group consisting of water, ethanol and mixtures thereof, optionally with heating, to form a drospirenone solution;
combining the cyclodextrin solution and the drospirenone solution to form a combined solution;
stirring the combined solution;
filtering the resultant precipitate;
washing the precipitate with a solvent selected from the group consisting of water, ethanol, ether and acetone;
optionally, suspending the resultant solid in a solvent and washing the suspended material with a solvent selected from the group consisting of water, ethanol, ether and acetone; and
removing substantially all of the solvent from the resultant or suspended material.

18. The method according to claim 17, wherein the removing of solvent is by spray drying.

19. The method according to claim 17, wherein the removing of solvent is by lyophilization.

20. The method according to claim 8, further comprising combining a therapeutically active substance other than drospirenone to the combined solution of drospirenone, to the drospirenone solution, or to the cyclodextrin solution.

21. A method for improving the solubility of drospirenone in water comprising complexing drospirenone with cyclodextrin to form an inclusion complex.

22. A pharmaceutical composition comprising an inclusion complex of claim 1 further comprising one or more pharmaceutically acceptable carriers or excipients.

23. The pharmaceutical composition according to claim 22 adapted to be administered by oral, parenteral, mucosal, topical, vaginal, subcutaneous or nasal administration.

24. The pharmaceutical composition according to claim 22, wherein the amount of drospirenone is from approximately 0.1 mg to 10 mg, per administration dose.

25. The pharmaceutical composition according to claim 22, wherein the complex further comprises one or more therapeutically active substances, other than drospirenone.

26. A method for female contraception comprising administering an inclusion complex as defined by claim 1 to a female.

27. A method for treating menopausal symptoms comprising administering an inclusion complex as defined by claim 1 to a female.

28. The method of claim 17, wherein the solvent used to wash the precipitate has been cooled to below 25° C.

29. The inclusion complex of claim 2, wherein the cyclodextrin is α-cyclodextrin, β-cyclodextrin or γ-cyclodextrin derivatized by being alkylated, acylated, benzylated or benzoylated at some or all of the primary or secondary hydroxyls of the macrocyle.

30. The inclusion complex of claim 1, wherein the complex is in the form of a hydrate containing between about 1% and 25% water.

31. The inclusion complex of claim 7, wherein the therapeutically active substance other than drospirenone is a steroid.

32. The inclusion complex of claim 7, wherein the therapeutically active substance other than drospirenone is an estrogen, progestogen or gestagen.

33. The pharmaceutical composition of claim 25, wherein the therapeutically active substance other than drospirenone is a steroid.

34. The pharmaceutical composition of claim 25, wherein the therapeutically active substance other than drospirenone is an estrogen, progestogen or gestagen.

* * * * *

UNITED STATES PATENT AND TRADEMARK OFFICE
CERTIFICATE OF CORRECTION

PATENT NO.    : 6,610,670 B2
DATED         : August 26, 2003
INVENTOR(S)   : Thomas Backensfeld et al.

It is certified that error appears in the above-identified patent and that said Letters Patent is hereby corrected as shown below:

Column 9,
Line 31, reads "according to 8" should read -- according to claim 8 --

Column 10,
Line 38, reads "of the macrocyle." should read -- of the macrocycle. --

Signed and Sealed this

Twentieth Day of July, 2004

JON W. DUDAS
*Acting Director of the United States Patent and Trademark Office*